US012245968B2

(12) United States Patent
Garvey (10) Patent No.: US 12,245,968 B2
(45) Date of Patent: Mar. 11, 2025

(54) INTRAORAL DEVICE WITH TOOTH CONTACT PREVENTION FEATURES (71) Applicant: Randal P. Garvey, Uhrichsville, OH (US)

(72) Inventor: Randal P. Garvey, Uhrichsville, OH (US)

(*) Notice: Subject to any disclaimer, the term of this patent is extended or adjusted under 35 U.S.C. 154(b) by 0 days.

(21) Appl. No.: 18/361,420

(22) Filed: Jul. 28, 2023

(65) Prior Publication Data
US 2025/0032308 A1 Jan. 30, 2025

(51) Int. Cl.
A61F 5/56 (2006.01)

(52) U.S. Cl.
CPC ........ A61F 5/566 (2013.01); A61F 2005/563 (2013.01)

(58) Field of Classification Search
CPC ...... A61F 5/56; A61F 5/566; A61F 2005/563; A61C 7/08; A61C 7/36
See application file for complete search history.

(56) References Cited

U.S. PATENT DOCUMENTS

| | | | | |
|---|---|---|---|---|
| 2,750,941 A * | 6/1956 | Cathcart | ............... | A63B 71/085 128/862 |
| 3,132,647 A * | 5/1964 | Corniello | ................ | A61F 5/566 D24/176 |
| 3,434,470 A * | 3/1969 | Strickland | ............... | A61F 5/566 128/848 |
| 3,871,370 A * | 3/1975 | McDonald | ............... | A61C 7/08 128/860 |
| 4,983,122 A * | 1/1991 | Mitnick | ................. | A61C 19/06 607/105 |
| 5,117,816 A * | 6/1992 | Shapiro | .................... | A61F 5/566 128/207.14 |
| 5,323,787 A * | 6/1994 | Pratt | ..................... | A61C 19/063 433/80 |
| 5,682,904 A * | 11/1997 | Stinnett | ................ | A63B 71/085 128/862 |
| 6,314,960 B1 * | 11/2001 | Vines | .................... | A61C 19/063 128/859 |
| 6,895,970 B1 * | 5/2005 | Lawrence | ............... | A61F 5/566 128/859 |
| 7,882,839 B2 * | 2/2011 | Ambis, Jr. | ........... | A63B 71/085 128/861 |
| 8,662,084 B2 * | 3/2014 | Thornton | ................. | A61C 7/36 128/859 |
| 2019/0336321 A1 * | 11/2019 | Garvey | .................... | A61F 5/566 |
| 2021/0068922 A1 * | 3/2021 | Nisi | ..................... | A61N 5/1014 |

* cited by examiner

Primary Examiner — Camtu T Nguyen
(74) Attorney, Agent, or Firm — Cynthia S. Lamon; Lamon Patent Services (57) ABSTRACT

An intraoral device includes a shell form including a top surface, a bottom surface, an arcuate anterior edge, a posterior edge and a nominal depth between the top and bottom surfaces thereof, an arcuate channel formed within the shell form along the anterior edge, open at the top surface, the channel including dental impression material enabled by process to accept a plurality of maxillary anterior teeth of a user forming a mold, a bottom plate assembled to the bottom surface of the shell form may be interchangeable, the bottom plate conforming to the peripheral shape of the shell form, the bottom plate hosting at least one incline angle on the bottom surface thereof.

8 Claims, 12 Drawing Sheets

INTRAORAL DEVICE WITH TOOTH CONTACT PREVENTION FEATURES

BACKGROUND OF THE INVENTION

1. Field of the Invention

The present invention is in the field of dentistry as it relates generally to an affordable over-the-counter intraoral device for the purpose of providing relief from the pain of Temporomandibular Disorder including Occlusal Muscle Disorder.

2. Discussion of the State of the Art

Temporomandibular disorder (TMD) includes conditions of occlusal muscle disorder and intracapsular disorder. These are common terms referring to the pain and dysfunction that results. TMD is a group of symptoms that can occur together which can be caused by anatomical factors, be precipitated by trauma, occlusal changes, or by abnormal or disordered functions referred to as parafunction such as bruxism and teeth clenching.

The mandible, or lower jaw, is articulated with the temporal bone at the temporomandibular joint (TMJ). The TMJ is a complex joint that allows for hinging or rotational action and for gliding or translational movement to open and close. Muscles and teeth related to the TMJ must interact in coordinated harmony to prevent or decrease muscle hyperactivity. If these elements do not function in harmony, pain and restricted movement may occur.

Common symptoms of TMD include muscle pain including trismus, clenching, grinding of teeth caused by muscle hyperactivity which may occur when the person is asleep or awake. Most experts strongly recommend treatments that are conservative. Some of these approaches include changing to a soft food diet, stretches and applying heat to painful areas. Other treatments may include medications such as anti-inflammatory drugs, muscle relaxants, anti-anxiety and antidepressant drugs; bite splints, mouth guards, or other appliances. Some professionals equilibrate the occlusion in order to remove an occlusal interference.

Muscles of the jaw can be defined as jaw elevators: the masseter, temporalis, medial pterygoid, and superior belly of the lateral pterygoid. Jaw depressors are identified as the anterior digastrics, geniohyoid, mylohyoid and inferior belly of the lateral pterygoid. During jaw opening, depressor muscles contract while elevator muscles release. During jaw closing the elevator muscles contract while the depressor muscles release contraction. Specifically, the inferior lateral pterygoid muscle contracts during jaw opening and releases during jaw closing.

Maximum intercuspation refers to the position of the mandible in which the cusps of the teeth of both arches fully interpose themselves with the cusps of the teeth of the opposing arch. When clenching with the condition of maximum intercuspation in centric relation and no posterior interferences, the inferior lateral pterygoid remains in the released or relaxed position.

The inventor of the present invention identifies the cause of TMD as a disruption in the coordinated manner the muscles contract and release, commonly caused by a posterior occlusal interference. Posterior occlusal interferences can be caused by many factors including deflective tooth contact, a condition of tooth contacts that divert the mandible from a normal path of closure. Additionally, a high crown, filling, or wearing of an incorrect, ill fitting mouth guard or other oral dental device may cause occlusal interference. Occlusal interference causes incoordination of and directly stimulates hyperactivity of the masticatory neuromuscular, discussed above. Occluso-muscle pain and headache often results rendering the condition of TMD. The specific cause of this pain is the fact that the fact that the masticatory neuromuscular contracts in an uncoordinated manner due to the occlusal interference.

When the mandible is not moving freely and occlusal interference is occurring, the automatic contraction moves the mandible forward causing the condyle of the mandible to move out of its natural position, which is seated in the fossa. This muscle contraction is an involuntary autonomic neuromuscular reaction to the interference and also happens when one is asleep. The automatic reaction is instigated in order to protect the system and remove the interference via grinding in an attempt to eliminate the interference and stop the muscle uncoordinated hyper contraction.

Various non-surgical devices are specifically designed to protect the teeth from damage resulting from TMD and OMD such as "splints", "mouth guards", or "night guards". Over the counter (OTC) mouth guards known in the art are soft full arch coverage devices that will not allow freedom of movement of the mandible. They allow or become posterior interference contacts that limit the mandibular position and cause muscle in-coordination, thereby limiting the relief that may be realized by these devices. Full coverage devices are known to become an occlusal interference when the full coverage device is not fabricated precisely and may cause muscle hyperactivity contraction. This can hold the mandible in a more forward position, not allowing the condyle to be retracted back into the fossa. This is an inappropriate, incorrect and ineffective way to relieve occlusal muscle pain caused by TMD. These devices actually keep the mandible from moving freely and exacerbate the condition and symptoms of TMD and OMD.

The inventor has provided an intraoral device comprising a shell including a top surface, bottom surface, an anterior edge, a posterior edge and a depth between the top and bottom surfaces, and a channel formed within the depth along the anterior edge, opening towards the top surface, the channel containing dental impression material enabled to accept a plurality of maxillary anterior teeth of a user. A smooth, rigid plane is formed on the bottom surface of the intraoral device shell and enabled to make contact with mandibular anterior teeth of the user. When the intraoral device is in place on the maxillary anterior teeth, the mandibular anterior teeth make contact with the smooth rigid plane of the device. When the jaw is in a closed position, the mandibular anterior teeth can move freely on the smooth rigid plane when there are no posterior interferences, thus relaxing the muscles and alleviating pain. However, it has occurred to the inventor that persons with overbites of varying degrees and malposed posterior teeth may still experience some occlusal interference at the posterior mandible induced by molar contact between the maxillary and mandible which may induce muscular discomfort and pain caused by hyperactivity and uncoordinated automatic contraction.

Therefore, what is clearly needed is an intraoral device with incline features added to the rigid plane according to the nature of the person's bite profile to maintain a gap between the maxillary and mandible to prevent occlusal interference in persons with varying degrees of overbite.

BRIEF SUMMARY OF THE INVENTION

According to an embodiment of the present invention, an intraoral device is provided comprising a shell form including a top surface, a bottom surface, an arcuate anterior edge, a posterior edge and a nominal depth between the top and bottom surfaces thereof, an arcuate channel formed within the shell form along the anterior edge, open at the top surface, the channel including dental impression material enabled by process to accept a plurality of maxillary anterior teeth of a user forming a mold, a bottom plate assembled to the bottom surface of the shell form, the bottom plate conforming to the peripheral shape of the shell form, the bottom plate hosting at least one incline angle on the bottom surface thereof. Movement of anterior mandibular teeth over the at least one incline toward the anterior edge increases a gap between the mandibular and maxillary molars along the bite plane and allows the lower mandible into a more relaxed, centric position.

In one embodiment, the bottom plate is assembled to the shell form and is interchangeable with bottom plates having at least one incline angle. In a preferred embodiment, the shell form is sufficiently wide to incorporate at least the maxillary incisors and adjacent canines of a user within the dental impression material. In a preferred embodiment, the bottom plate is assembled to the bottom surface of the shell form using pegs extending from the bottom plate and peg openings on the bottom surface of the shell form. Also in a preferred embodiment, the at least one hosted incline angle is contiguous with the material of the bottom plate.

In one embodiment, the at least one hosted incline angle is a wedge form centered on the bottom plate, the incline angle creating a uniform height dimension at the anterior edge of the wedge form along the width dimension of the wedge form. In a separate embodiment, at least one hosted incline angle is an angular lip formed contiguously along the curved anterior edge of the bottom plate. In a variation of this embodiment, the angular lip has an incline that is radiused slightly to prevent a hard stop at the beginning of the incline.

In a preferred embodiment, the wedge form has a nominal incline angle within a window of angles ranging from about five degrees to about twenty five degrees from horizontal. In one embodiment, individual ones of the interchangeable bottom plates are provided as a set each individual plate having a different incline angle. In one embodiment, the interchangeable bottom plate hosing an incline angle of about twenty five degrees is assembled to the shell form of a user having a maximal pronounced overbite and wherein the interchangeable bottom plate hosting an incline angle of about five degrees is assembled to the shell form of a user having a minimal overbite.

DETAILED DESCRIPTION OF THE INVENTION

The present inventor identifies and addresses a problem in the art not considered by current art professionals when developing devices that only address the symptoms of TMD. As previously presented, the actual root cause of TMD and OMD, specifically, is a disturbance in the coordinated muscle function of masticatory musculature controlling the mandible, condyle and articular disc. Only when the mandible is left to translate freely during treatment can the root cause of TMD and OMD be corrected.

Figure 1A:
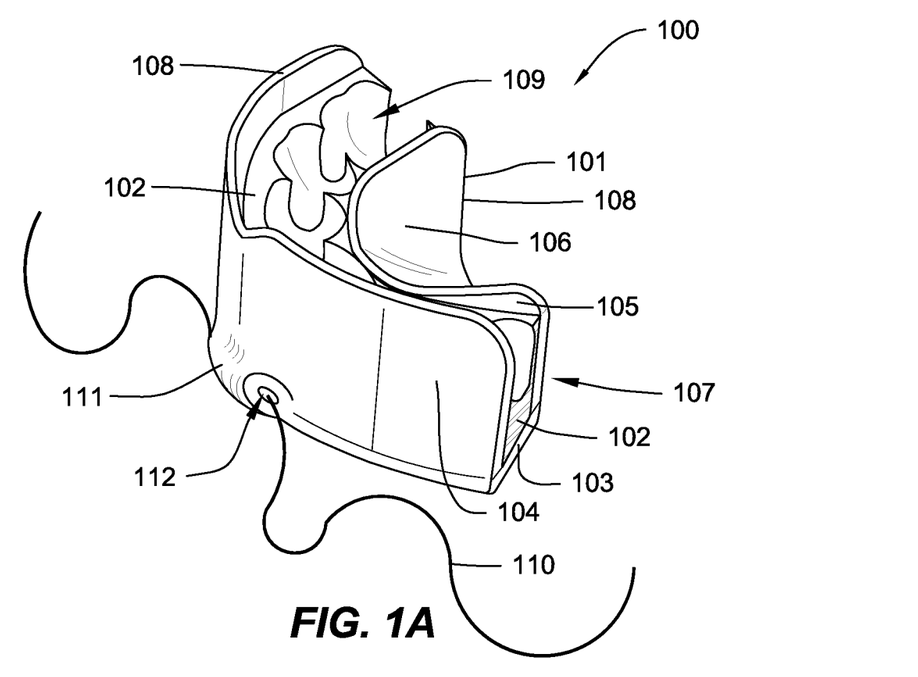
FIG. 1A is a perspective view of the intraoral bite plane device showing the device after the dental impression material has been customized by the user.
Figure 1B:
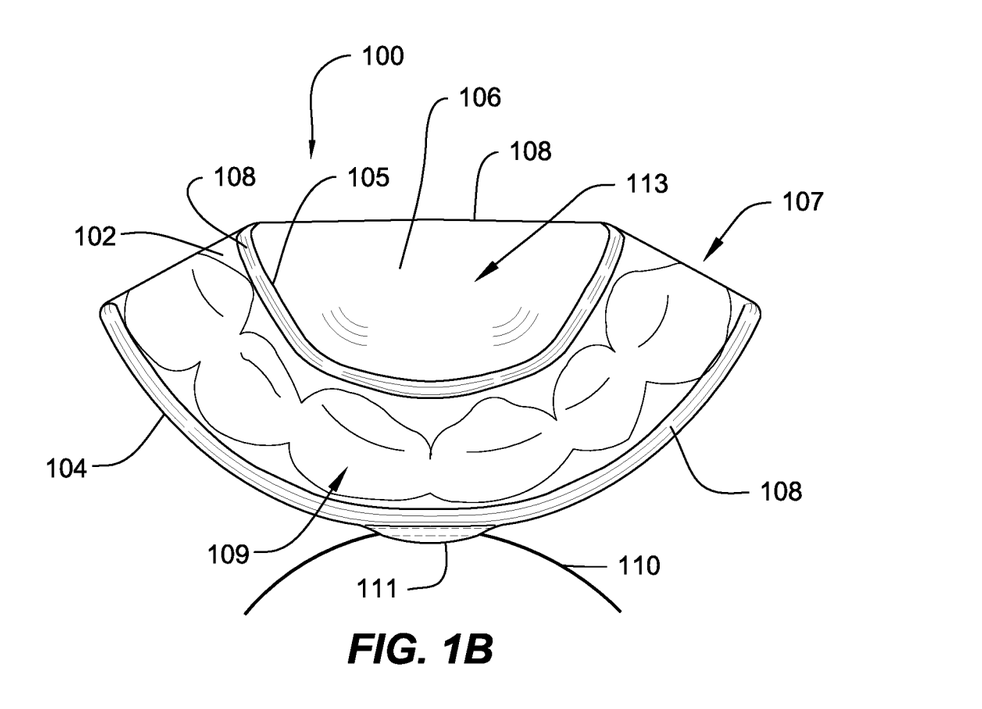
FIG. 1B is a plan view of the intraoral bite plane device customized by the user.

FIGS. 1A and 1B depict a preferred embodiment of an OTC intraoral device 100 providing relief from acute discomfort of temporomandibular dysfunction (TMD) at a lower cost, without waiting for a dental appointment. Device 100 is comprised of an outer shell 101, dental impression material 102, and a smooth flat rigid plane 103. Shell 101 is comprised of curved outer channel wall 104 which is slightly larger than and parallel to the labial or outside surface of the upper teeth; curved inner channel wall 105 slightly smaller than but parallel to the lingual or inside surface of the upper teeth; and a curved transition surface 106 situated within wall 105 sloping down to the posterior edge of plane 103.

Walls 104 and 105, may be joined with plane 103 during fabrication of device 100 by molding, by adhesion, by over molding, or other manufacturing processes. These elements form channel 107 into which a predetermined amount of material 102 is placed by the manufacturer. When impression material 102 is heated to become formable, for example, in hot water, impressions 109 of the teeth are made in the material, as described later. This material may be heated and reheated as necessary, or may be heated and formed one time.

All exposed edges 108 of device 100 shall be formed to a smooth radius to prevent irritation to the user's cheeks, gums, and tongue. Device 100 is equipped with an adjustable tether 110 that surrounds the head while device 100 is in use so that it can be retrieved if dislodged and swallowed or aspirated. Tether 110 shall be manufactured of medical grade silicone cord or similar flexible material. Tensile strength of tether 110 could be low enough that there is no danger of strangulation. A tether attachment tab 111 with cylindrical hole 112 allows the tether to be secured to device 100. The tether may be replaced if it is broken. Tether 110 is not shown in remaining figures to reduce confusion. Space 113 may provide a comfortable space for the user's tongue.

Figure 2A:
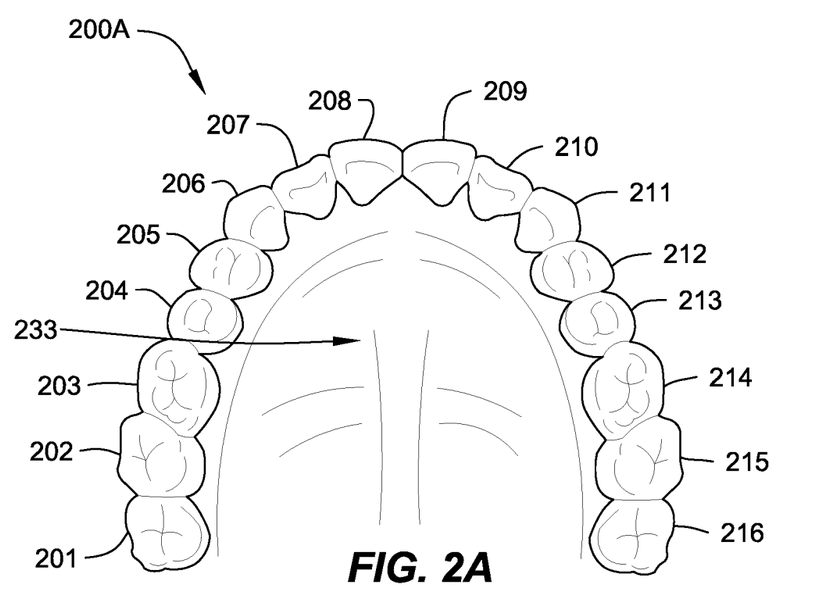
FIG. 2A provides a bottom view of the maxillary teeth and palate.

FIG. 2A identifies the maxillary or upper teeth 200A. Teeth 200A starting at the anterior center include: Central incisors 208 and 209, lateral incisors 207 and 210, cuspids, canine or eye teeth 206 and 211, first premolars or first bicuspids 205 and 212, second premolars and second bicuspids 204 and 213, first molars 203 and 214, second molars 202 and 215, and third molars 201 and 216 or wisdom teeth. The hard palate 233 or "roof" of the mouth is indicated as shown.

Figure 2B:
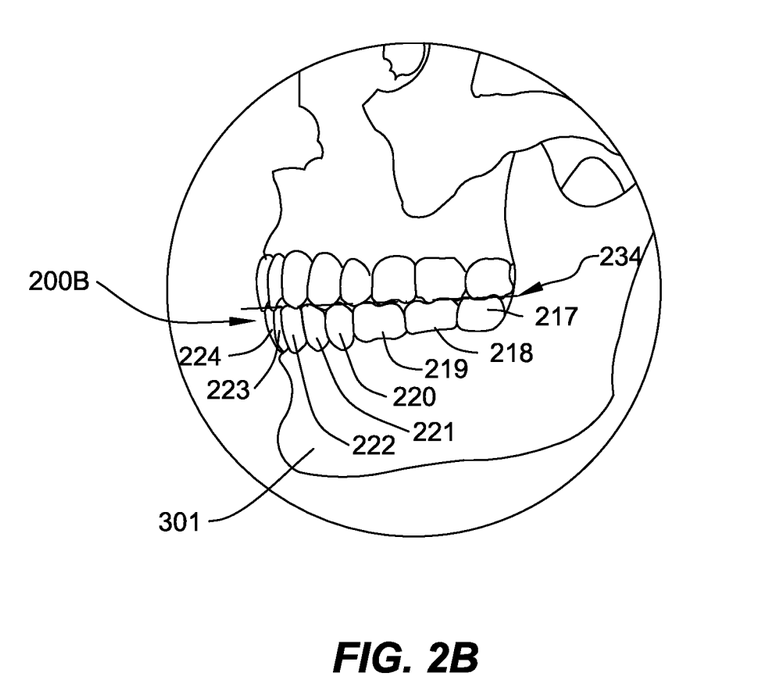
FIG. 2B is a left side view of the jaw, and identifies the left mandibular teeth.

Likewise, FIG. 2B identifies in a side view of mandibular or lower teeth 200B, left side only; starting at the front are the left central incisor 224, lateral incisor 223, cuspid or canine 222, first premolar 221, second premolar 220, first molar 219, second molar 218, and third molar 217. Corresponding mandibular teeth on the right side of the mouth are not shown in this view. The mandible or lower jaw is shown at 301. The occlusal plane 234 indicated in this figure is the plane that is formed by the occlusal surfaces of the teeth. Occlusal plane 234 is important when considering the function of the TMJ and in planning treatments to optimize the outcome for patients. This occlusal plane will be referred to again in later figures.

Figure 3A:
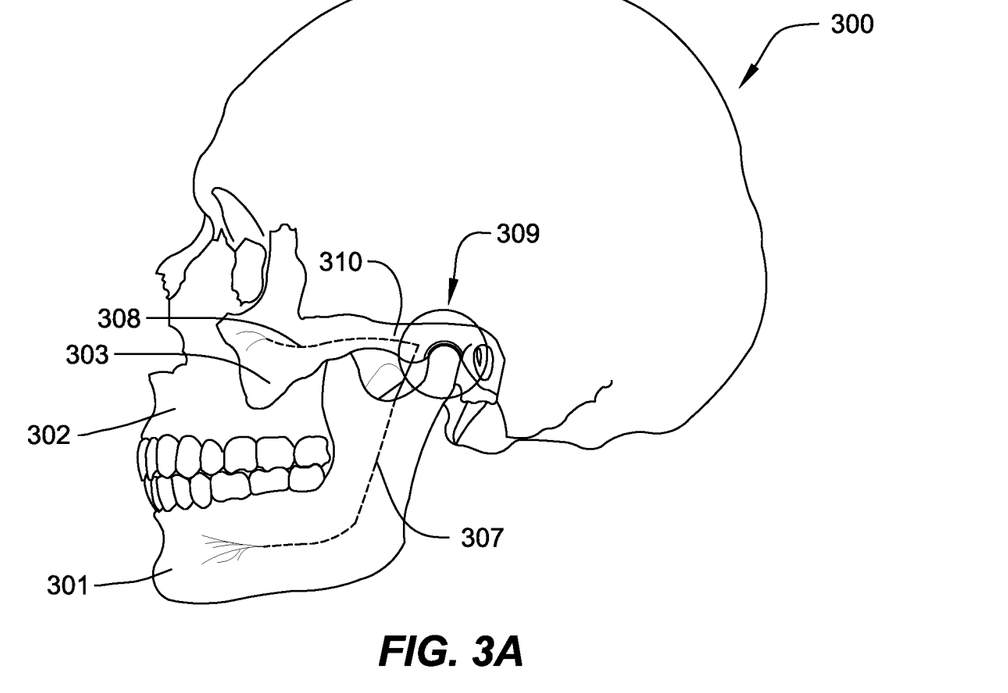
FIG. 3A is a left side view of the skull identifying bone structure of the jaw area.
Figure 3B:
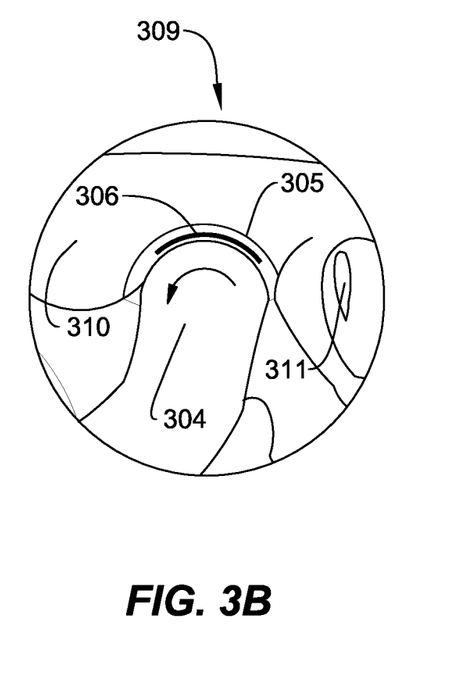
FIG. 3B provides an enlarged left side view of the temporomandibular joint in a closed or relaxed position.

FIG. 3A shows a left side view of the human skull 300. Identified thereon are the mandible or lower jaw 301, the maxilla 302, and the zygomatic bone 303. The right side of the skull has the same corresponding features which are not shown. Mandible 301 has a curved arch form, with wide ramus portions which extend from the angles of the mandible upward toward the temporomandibular joint on each side in front of ear openings 311 (FIG. 3B). Mandible 301 moves while talking, eating, clenching or grinding. Mandible 301 supports lower teeth 200B and shapes the chin and jowl areas of the face. Maxilla 302 supports upper teeth 200A. Zygomatic 303 shapes the cheek. Mandibular nerve 307 and maxillary nerve 308 run along the inside of mandible 301 and maxilla 302 until they surface outside of 301 and 302 and branch off into numerous smaller nerves as indicated. Nerve 307 innervates the muscles of mastication which are identified later in FIG. 4. TMJ 309 is indicated in this view and further detail is shown in the following figures.

FIG. 3B provides an enlarged left side view of joint 309 when it is in a relaxed state, such as when the jaw is closed and in a fully seated position where the condyle sits wholly in the fossa. Mandible 301 (FIG. 3A) articulates with the temporal bone in front of ear opening 311. Condyle 304 tapers in width and ends in a rounded head as shown. Temporal bone 310 is joined to zygomatic 303 by an oblique suture. Bone 310 continues along the high side of the check over opening 311. In front of opening 311, bone 310 has a concave depression that is the glenoid fossa 305. In the upper most position (centric relation) condyle 304 is positioned and braced against the temporal bone under the disc inside fossa 305. Articular disc 306 is a thin disc of non-vascular fibrous connective tissue that provides a cushion between condyle 304 and fossa 305. As mandible 301 opens slightly, it rotates about condyle 304 as indicated in this figure by the rotational arrow. As the opening increases condyle 304 begins its forward translation.

Figure 3C:
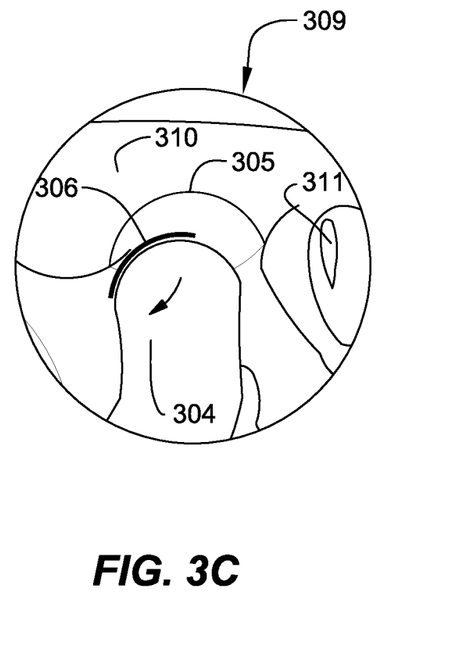
FIG. 3C provides an enlarged left side view of the temporomandibular joint in an open position with the condyle and articular disc displaced from the glenoid fossa.

FIG. 3C provides an enlarged left side view of joint 309 when it is in an open normal physiologic state. This view shows that mandible 301 translates down and forward on the disc as indicated by the arrow in this figure. Condyle 304 and disc 306 slide out of fossa 305 as shown. Joint 309 has a fibrous capsule surrounding the joint and a number of ligaments associated with the structure of the joint which are not shown in these figures. Stretching of those ligaments may cause corresponding symptoms such as popping, clicking, grating noises, tinnitus, and ear pain. The posterior of disc 306 is attached to fossa 305 with retrodiscal tissue not shown in the figures. The retrodiscal tissue is vascular and highly innervated. It can be painful if it is inflamed or compressed when the disc is displaced in a forward position in the joint. If inflammation lasts long enough an adhesion and scar tissue may form causing more pain.

Figure 4:
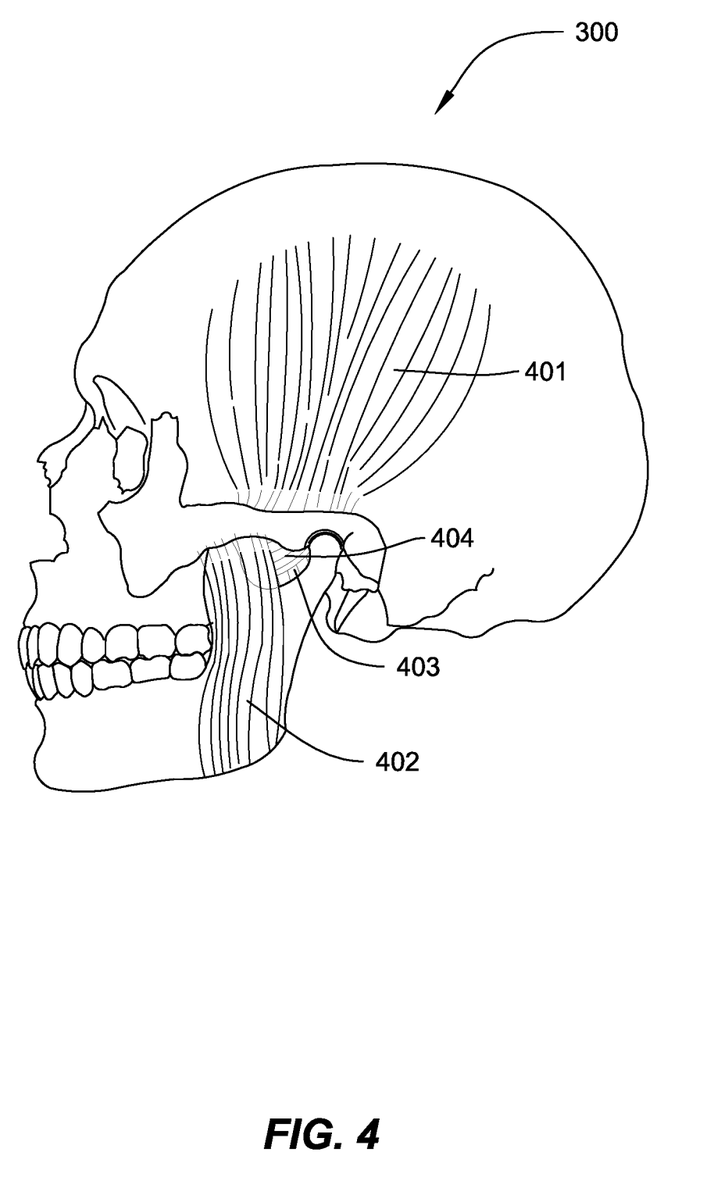
FIG. 4 shows a left side view of the skull and the four primary muscles of mastication.

FIG. 4 shows skull 300 and depicts the four primary muscles of mastication which are temporalis muscle 401, masseter muscle 402, medial pterygoid muscle 403, and lateral pterygoid muscle 404. Muscles 403 and 404 are both situated on the inside surface of mandible 301 so only a small portion can be seen in this figure. Muscle 402, together with muscle 403, form a sling around mandible 301. Muscles 401, 402 and 403 are used to adduct or raise the jaw. Muscle 404 protrudes the mandible and the disc in a coordinated movement. As indicated in the previous discussion of FIG. 3A, nerve 307 innervates these muscles of mastication.

Figure 5A:
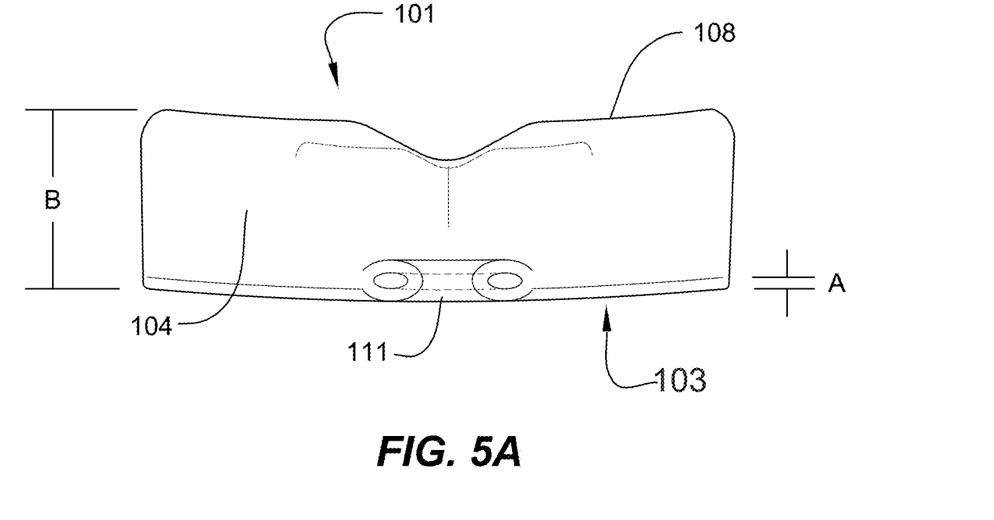
FIG. 5A is a front view of the shell of the device.

FIG. 5A provides a front view of shell 101 without material 109. Rigid plane 103 forms the bottom of device 100 and may be constructed of a medical grade polymer material with rigidity such that the plane will not flex under pressure when in use. The surface of plane 103 should be smooth to the point of providing little or no resistance to upper edges of the bottom anterior teeth that make contact with it, thus allowing the upper edges of the teeth to translate freely. There are a variety of materials that may be used to manufacture the plane 103 including, but not limited to enamel, acrylic, and synthetic polymers and resins with a smooth glass-like surface and durable enough to withstand continued contact from enameled teeth. Some metals are smooth enough to allow the lower anterior teeth to make contact and slide freely as well, including polished titanium and stainless steel.

Dimension A is the thickness of plane 103 which should be minimized to avoid adding bulk to device 100. Dimension A could range from 0.5 mm to 1.5 mm depending on specific type of material used. Materials comprising walls 104 and 105 (not shown in this view) and the mass forming surface 106 may be constructed of medical grade polymer however this material may be slightly malleable to make device 100 more comfortable for the user. Dimension B is the height of wall 104. This height may be in the range of 6 mm to 8 mm; it will not rise above the labial gingival margin of teeth 200 to minimize user discomfort or tissue irritation.

Figure 5B:
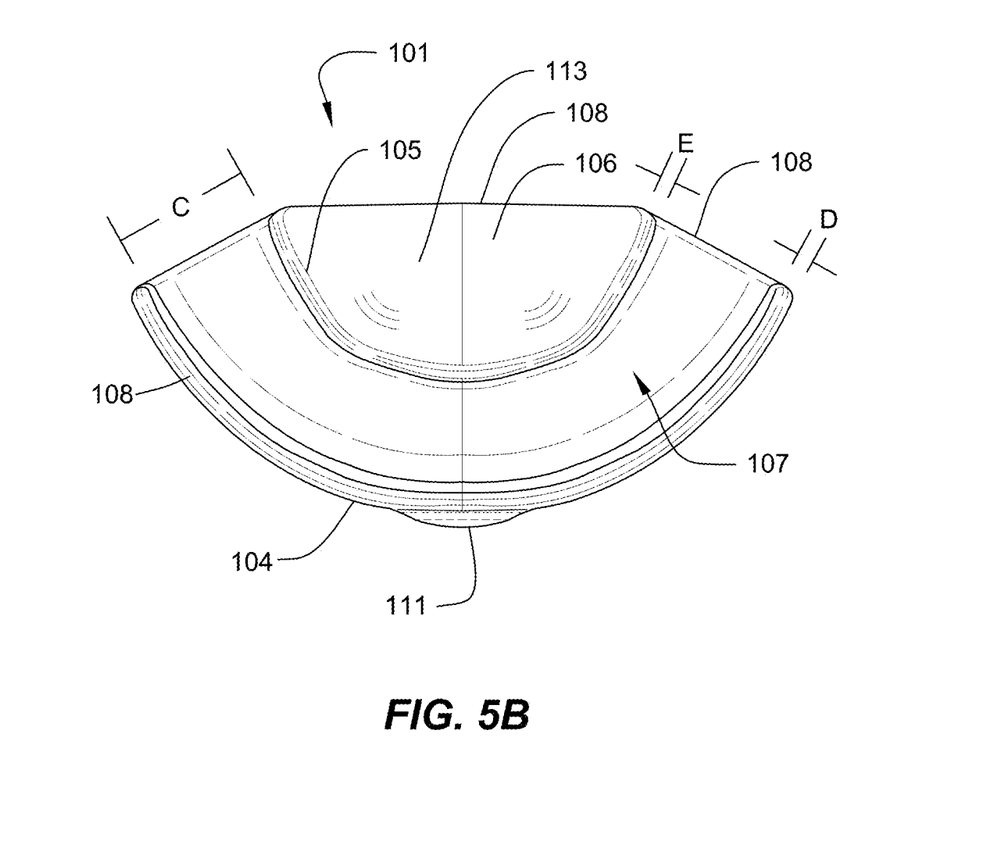
FIG. 5B is a plan or top view of the shell of the device.
Figure 6A:
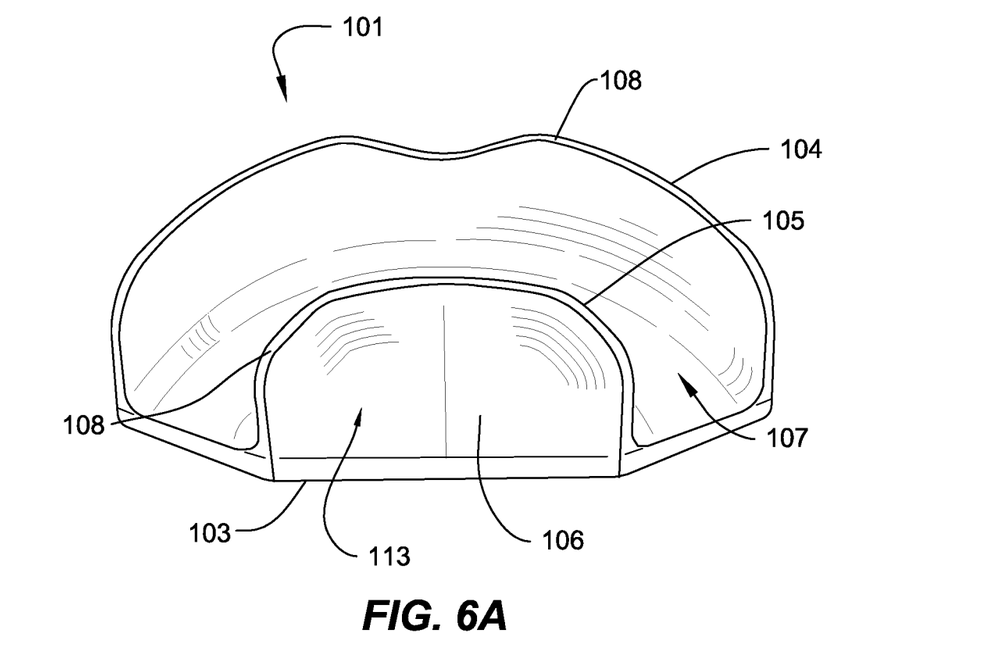
FIG. 6A is a posterior top view of the shell of the device.
Figure 6B:
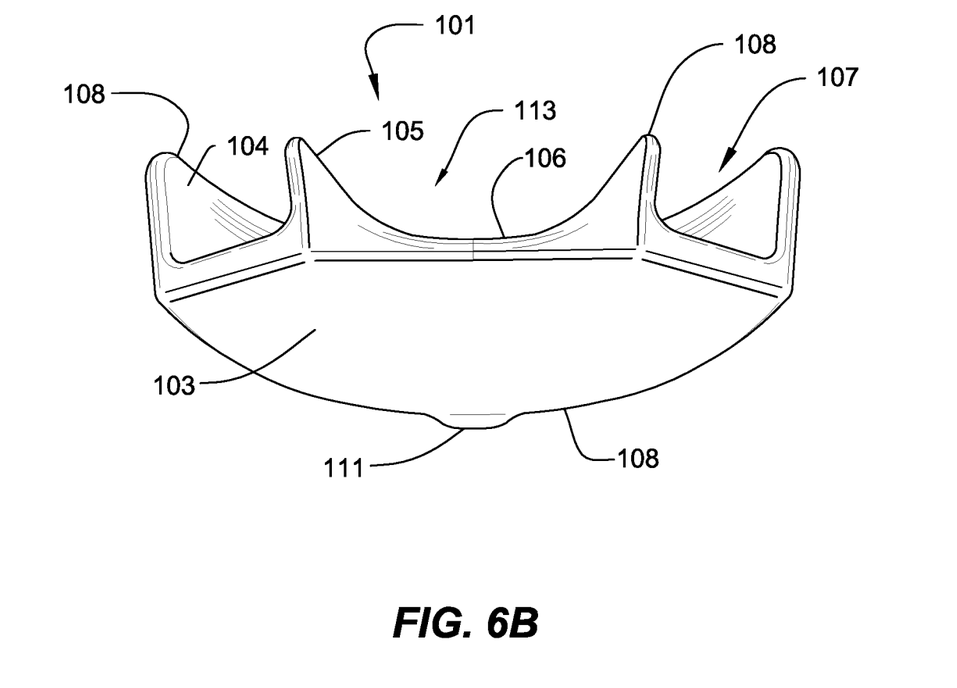
FIG. 6B is a posterior bottom view of the shell of the device.

FIG. 5B shows a plan or top view of shell 101. The outline of shell 101 is the same shape as plane 103 which forms the underside of device 100. Plane 103 cannot be seen in this view but is shown in FIG. 5A above. As can be seen in FIG. 5B, walls 104 and 105 are arranged along arcs which parallel just inside and outside of upper teeth 200 (FIG. 2A) respectively. Dimension C is the width of channel 107 formed by walls 104 and 105 and plane 103 which encompasses the six anterior maxillary teeth 206-211. FIG. 1B outlines these teeth as impression 109. Walls 104 and 105 extend to the inter-proximal or inter-dental interface between teeth 205 and 206 and between teeth 211 and 212. Tab 111 can be seen in this view. The tab is rounded and smooth in all directions to prevent irritating contact with the user's lips. Dimension D is the thickness of wall 104 which may be in the range of 1 mm-3 mm but may be the minimum required to retain the shape of channel 107 during the forming process described later herein. Wall 105 is supported by the mass of material which forms surface 106. Dimension E depicts the thickness of wall 105 which may be formed with a radius and thickness as dimension D. FIGS. 6A and 6B show shell 101 from posterior above and below to provide clearer understanding of the geometry of device 100. Space 113 is more clearly shown in this view. The user may extend the tongue if needed in space 113 above device 100 between surface 106 and palate 233, or below plane 103 in the space surrounded by lower teeth 200B.

Figure 7A:
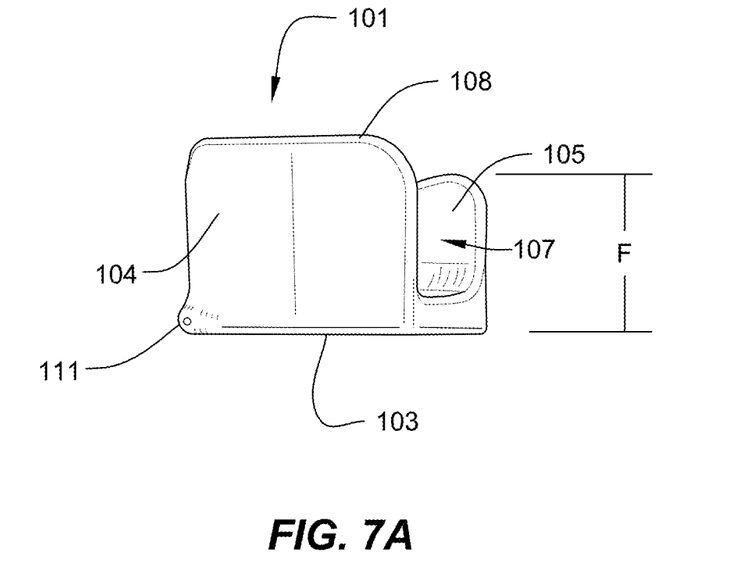
FIG. 7A is a left side view of the shell of the device.

FIG. 7A provides a left side view of shell 101. Dimension F is the height of wall 105. As can be seen, dimension F is less than dimension B on FIG. 5A and may be in a range of 4 mm to 7 mm. Wall 105 is lower than wall 104 because the gingival margin on the lingual side of teeth 206-211 is lower than on the labial side.

Figure 7B:
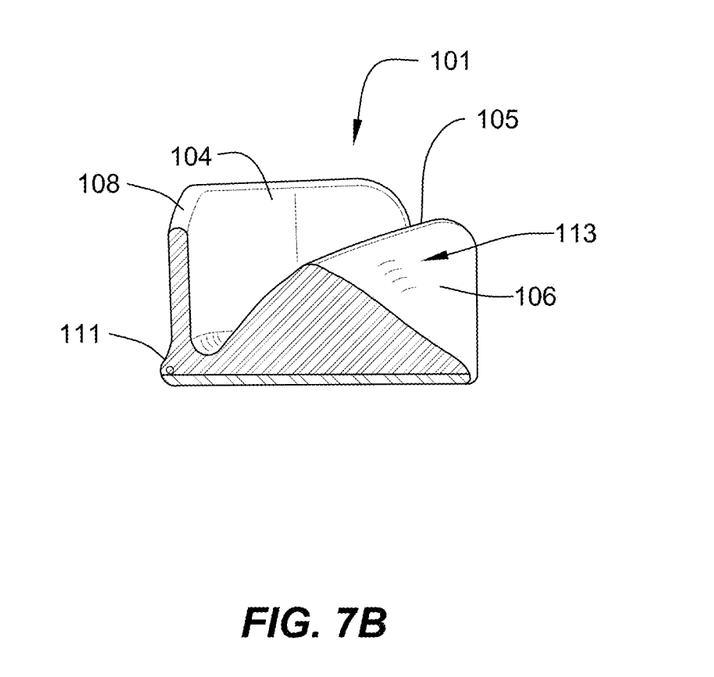
FIG. 7B is a left side section view of the shell of the device.

FIG. 7B is a left side section view of shell 101 cut along the front to back center line. This figure provides additional clarification of the contour of surface 106 and space 113. In this view the device is placed over teeth 206-211. More or less teeth may be incorporated in the device while still enabling regular function of the teeth as understood by one with skill in the art. For example, device 100 may only incorporate teeth 207-210 or 205-212.

Figure 8A:
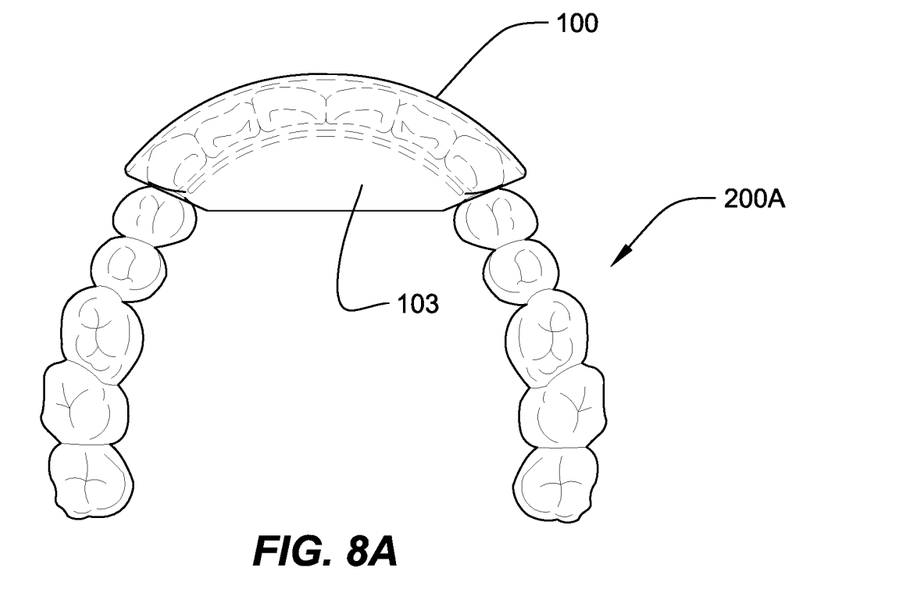
FIG. 8A provides a bottom view of the device in place on the anterior maxillary teeth.

FIG. 8A provides a bottom view of maxilla 202 and teeth 200A with device 100 properly in place. Surface 103 is toward the viewer. As shown in this embodiment, the device covers teeth 206-211 (FIG. 2A).

Figure 8B:
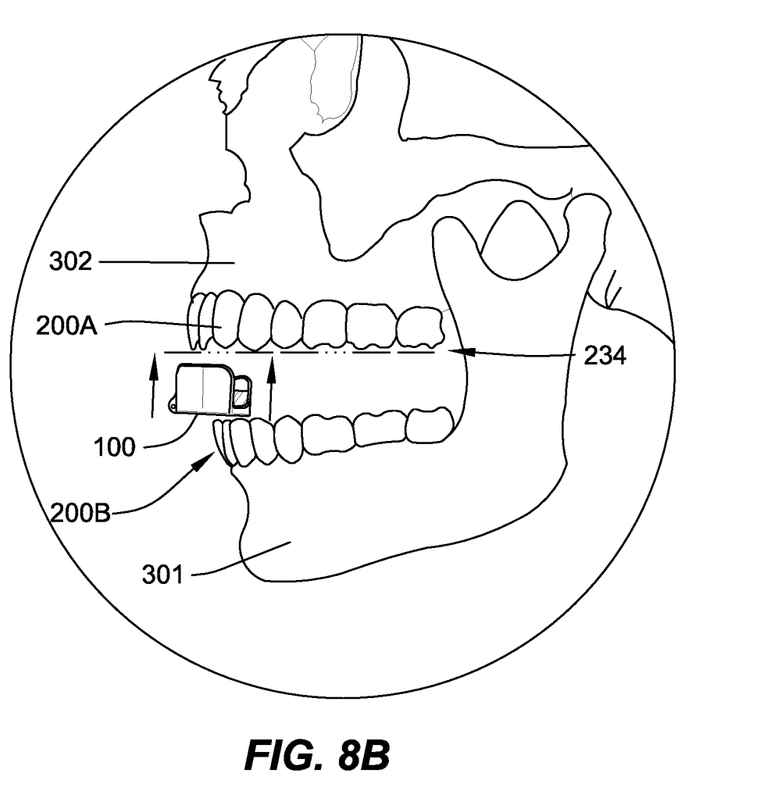
FIG. 8B shows a left side view of the device prepared and aligned to form the teeth impressions.

FIG. 8B shows a left side view wherein device 100 is ready to fit to the user. Shell 101 is shown with a previously measured volume of material 102 in channel 107. The amount of material is selected to fill the channel 107 more than half the depth of the channel in order to cover the teeth when formed to an extent that holds the device 100 on the teeth securely.

The user may heat device 100 in a microwave or in hot or boiling water to soften material 102, depending upon the type of material used. After a recommended period of time to cool device 100 and material 102 to a safe temperature, device 100 is inserted into the mouth placing it over teeth 206-211, in this embodiment, and pressing device 100 firmly in place in the direction of the arrows shown. Surface 103 may be oriented to align as closely as possible with plane 234 for proper fit. The user may use thumbs to hold device 100 in place while material 102 continues to cool and become firmer based on manufacturer recommendations. Material 102 shall be of medical grade thermoplastic with a low enough melting point that it can formed at a low enough temperature that it is safe to handle and to use to create the impressions. Thermoplastic material may be used that can be reheated and reformed in the event the user does not initially achieve the desirable fit the first time.

Figure 9A:
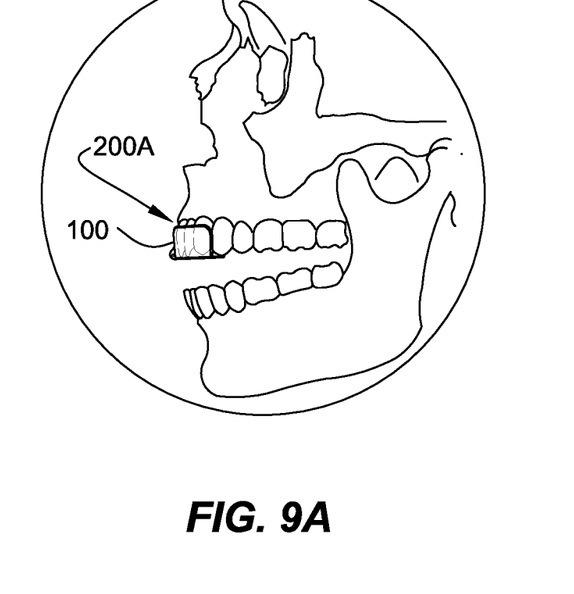
FIG. 9A shows a left side view of the device in place over the anterior maxillary teeth during forming and when in use.

FIG. 9A is a left side view showing device 100 properly situated over anterior teeth 206-211 in this embodiment. Displacement of material 102 by teeth 206-211 create impressions 109 which snugly fit around teeth securing device 100 in place during use. The previously measured volume of material 102 will be such that it is not pressed against the gums to avoid discomfort but will sufficiently encompass and provide secure fit around the affected teeth.

Figure 9B:
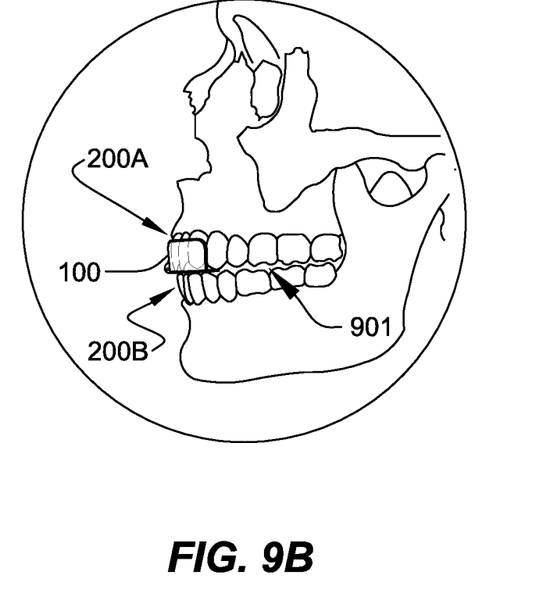
FIG. 9B shows a left side view of the device in place over the anterior maxillary teeth with the anterior mandibular teeth resting against the flat underside of the device.
Figure 10A:
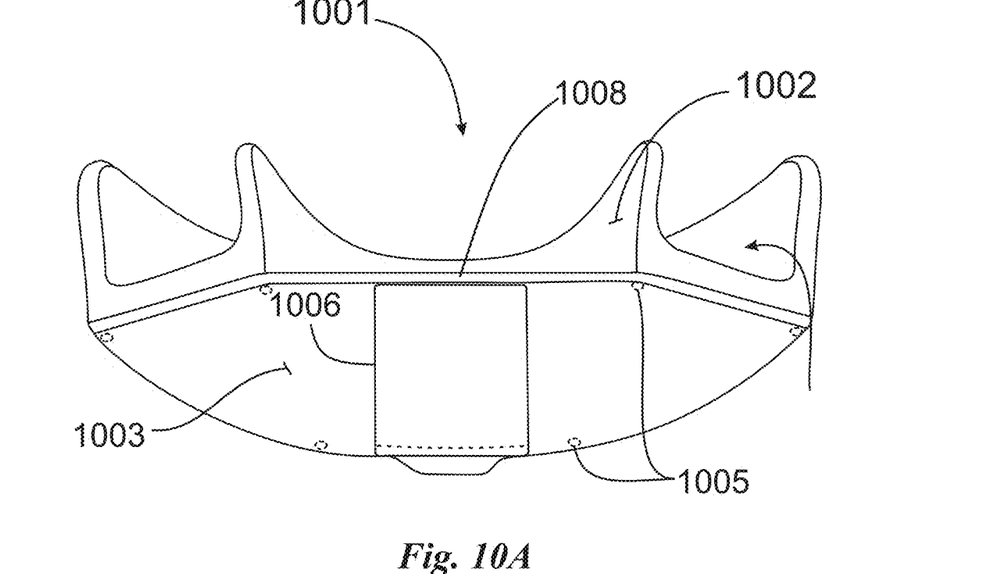
FIG. 10A shows an underside perspective view of an intraoral device similar to the device of FIG. 6B with added modifications according to an embodiment of the present invention.

FIG. 9B is a left side view showing device 100 in place with any or all of the anterior mandibular teeth making contact with plane 103 of device 100. The thickness of plane 103 together with the irregularities of the occlusions of lower teeth 222-225 in contact with the plane hold the mandible and maxilla slightly apart, creating an interocclusal space 901 between the maxillary and mandibular premolars and molars. In this position, muscles 401-404 are able to relax and condyle 304 and disc 306 return to a natural position in relation to fossa 305. Additionally, the mandible retains its freedom of movement. Only with an OTC device as provided by the present inventor, can the muscles of mastication relax into coordinated function, while maintaining complete freedom of movement of the mandible and all components included in 309. The benefits realized by the present invention includes stopping uncoordinated muscle hyperactivity by parting the back teeth thus eliminating premature interferences of posterior (back) teeth in centric relation. The flat, smooth, rigid plane allows freedom of movement of the mandible (permissive). Therefore, when the muscle in-coordination is eliminated, the mandible is free to move and be seated correctly in the fossa. When the muscle hyperactivity and in-coordination is eliminated, the muscle pain subsides. The muscles relax and muscle splinting subsides. When the muscle in-coordination and hyperactivity is eliminated, the disc is allowed to be pulled back (posteriorly) into a more normal position onto the head of condyle, or at least help keep the disc from being pulled more forward in the early stages of TMD. Device 101 can stop or slow down the progression of TMJ internal derangement. Because the posterior teeth are held apart, they are protected from injury (fracture), wear, and bone loss from heavy occlusal forces from systemic and nocturnal bruxing or clenching caused by the hyperactivity. FIG. 10A shows an underside perspective view of an intraoral device similar to the device of FIG. 6B with added modifications according to an embodiment of the present invention.

Intraoral Device customized for Overbite Profiles

It is the goal of the present invention to provide an intraoral device that may be further customized to a user who has a degree of overbite that poses a risk of occlusal interference defined by potential contact between the maxillary and mandible posterior molars in lateral or protrusive mandibular movements. It is a goal of the invention to introduce an incline at the underside of the bottom plate of the intraoral device adapted to maintain a healthy gap in the bite plane between maxillary and mandible molars for persons with an overbite profile.

FIG. 10A shows an underside perspective view of an intraoral device 1001 similar to the device 101 of FIG. 6B with added modifications according to an embodiment of the present invention. Intraoral device 1001 may be manufactured of the same materials described for the manufacture of device 101. In this embodiment, a shell form 1002 may be a one piece contiguous form molded for a general maxillary anterior position and arc of the device for a user. Dental impression material is removed from this view for clarity but may be assumed present and analogous in position and form to dental impression material 109 of FIG. 1A.

Intraoral device 1001 includes a bottom plate 1003 that forms the under surface of the device and is referred to as a smooth, flat, and rigid plane separating the anterior mandible and maxillary teeth, particularly incisors and canines. A unique aspect of the present invention is a design feature that enables bottom plate 1003 to be removed from shell form 1002 such that they are two separate parts of intraoral device 1001. In this embodiment, the anterior centric bite plane may be considered identical to the same for intraoral device 101 described further above. Bottom plate 1003 may be manufactured from a variety of different materials like thermoplastics, carbon fibers, titanium, acrylics, or similar non-toxic materials.

In this embodiment, bottom plate 1003 may be assembled to shell form 1002 using peg in hole interfaces 1005 of which there are three to six depicted strategically disposed about the perimeter edge of the bottom plate whereby pegs on the bottom plate 1003 snap into an aligned pattern of peg openings placed into the bottom surface of shell form 1002. In one embodiment, bottom plate 1003 supports a wedge-form 1006. Wedge form 1006 may be a rigid or semi-rigid polymer form or thermoplastic form roughly centered on plate 1003 proximal to the anterior edge of the plate and the wedge incline tapers to a posterior edge of the plate. Wedge form 1006 may be formed onto bottom plate 1003 via heat weld, or it may be a contiguous form molded with the plate material. In a preferred embodiment, wedge form 1006 is not removable from bottom plate 1006 to avoid the possibility of choking if the part came loose while the intraoral device is being used.

Wedge form 1006 has a positive incline slope beginning at or near the rear edge of intraoral device 1001 and progressing out from the plate surface toward the anterior edge of the intraoral device 1001. Bottom plate 1003 and wedge form 1006 may be removed from shell form 1002 and another bottom played with a wedge form having a different slope angle may be provided for replacement. The angle of the incline for a wedge form like wedge form 1006 may be provided within a range from a 5-degree angle up to a 20 degree angle providing a range of adjustment angles to compensate for slight to heavier overbite profiles of users. In one embodiment, bottom plate 1003 with wedge form 1006 may be swapped out for another bottom plate having a wedge form of a differing incline angle during fitting of the intraoral device to a particular user's overbite. In this way, the same shell form can be used for a patient with a specific bottom plate having a wedge form that matches the overbite profile of that person. For a person with a slight overbite, a smaller wedge form incline angle is desired whereas a person with a maximum overbite may require a wedge form with a much greater incline angle like 20 degrees.

The central position of wedge form 1006 with the incline progressing toward the anterior edge of the intraoral device provides a slope for mandibular incisors to be resistant to forward translation as muscles relax, thereby guiding the mandible into centric relation.

Figure 10B:
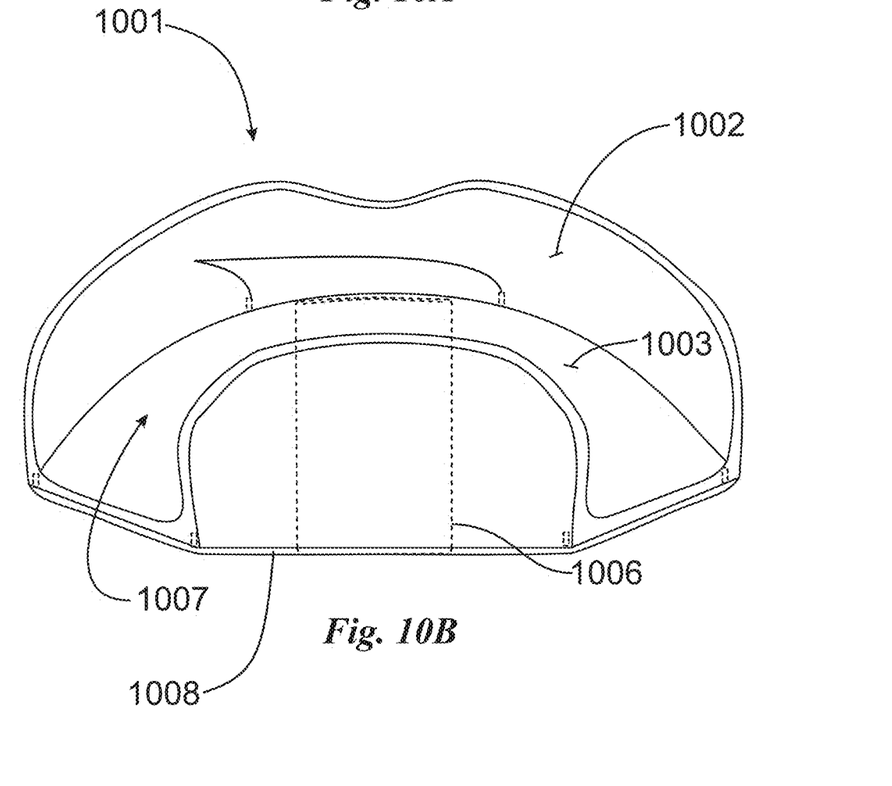
FIG. 10B shows an overhead perspective view of the intraoral device of FIG. 10B.

FIG. 10B shows an overhead perspective view of the intraoral device of FIG. 10A. In this view, the internal volume of trough 1007 is visible. Dental impression material like material 109 of FIG. 1A may be assumed present. The method for customizing the device to a user using the dental impression material may be identical to the method described further above in the parent application disclosure that references heating the material before maxillary tooth impressions are made in the material. It is noted herein that the height of wedge form 1006 toward the anterior edge of bottom plate 1003 depends on the given angle of the incline and the total length of the wedge form.

Attachment interfaces 1005 are depicted as pegs (broken boundary) extending into the peg openings provided for the purpose on the bottom surface of shell form 1002 about the perimeter edge thereof. Other attachment means for assembling bottom plate 1003 to shell form 1002 may be observed and implemented without departing from the spirit and scope of the present invention. In an alternative embodiment, wedge forms like wedge form 1006 may be provided to attach to bottom plate 1003 whereby the bottom plate is permanently part of the shell form or molded in one contiguous form without departing from the spirit and scope of the present invention. In the just mentioned case, wedge forms may be swapped out for other wedge forms of differing inclines instead of switching out the bottom plates with the wedge forms permanently attached thereto. However, the embodiment is not preferred due to safety concerns of possible choking as explained further above.

Figure 11A:
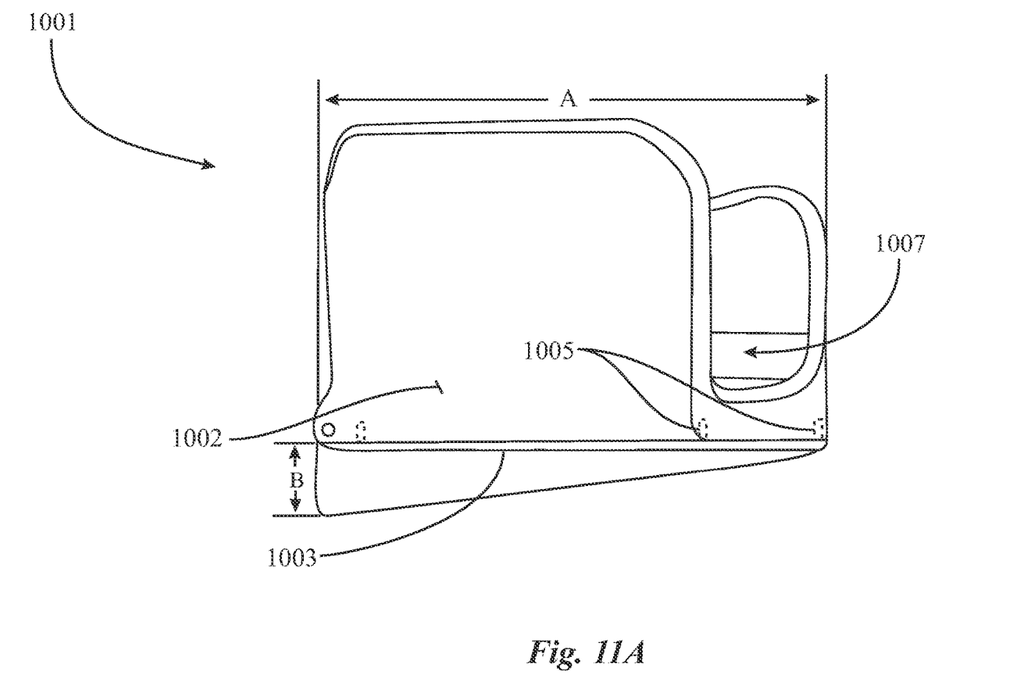
FIG. 11A shows a side view of the intraoral device of FIG. 10A.

FIG. 11A shows a side view of the intraoral device of FIG. 10A. Intraoral device 1001 is assembled and depicted in a side view to show the profile and position of wedge form 1006 formed on the bottom surface of bottom plate 1003. Bottom plate 1003 is assembled to the bottom of shell form 1002 using peg and hole interfaces 1005 depicted in a side view with pegs outlined in broken boundaries.

An overall length A from the anterior edge of the intraoral device 1001 to the posterior edge thereof may be about 24 millimeters, in one embodiment. Length A may be larger or smaller dependent on the arc and number of teeth covered by the intraoral device without departing from the spirit and scope of the present invention. The incline angle of wedge form 1006 begins in this example at the posterior edge of plate 1003 and rises in a gradual slope. Thus, the height C of the anterior edge of wedge form 1006 may be about 8 millimeters. The incline angle still allows free movement of the user's lower mandible, but as the mandible slides to the anterior edge, it encounters resistance because of the increasing slope and is guided back to a relaxed, natural position. Unintentional clenching and tooth grinding, or pressure contact may be avoided. Trough 1007 accepts the dental impression material (not illustrated) to enable the user to customize the intraoral device to their particular tooth profile and arc.

Figure 11B:
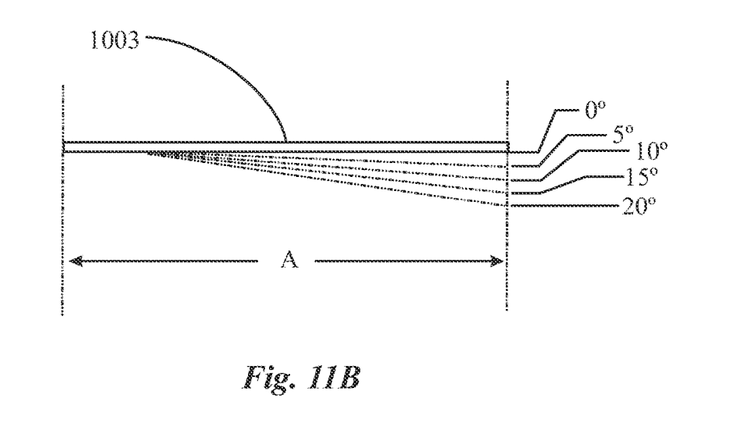
FIG. 11B shows a diagram depicting optional angles of incline for the wedge form of the intraoral device of FIG. 10A.

FIG. 11B shows a diagram depicting a side view of bottom plate 1003 and optional angles of incline for wedge form 1006 of intraoral device 1001 of FIG. 10A. Dimension A references the overall length of the intraoral device. In this embodiment incline angle options may be 0 degrees (no wedge form) 5 degrees, 10 degrees, 15 degrees, and 20 degrees. In one embodiment an intraoral device like device 1001 with interchangeable plates having wedge forms at different incline angles may add protection and comfort to the patient faced with TMD symptom concerns. In an alternative embodiment, incline angles may be produced in the bottom plates without requiring a separate wedge form to be added to the intraoral device.

Figure 12A:
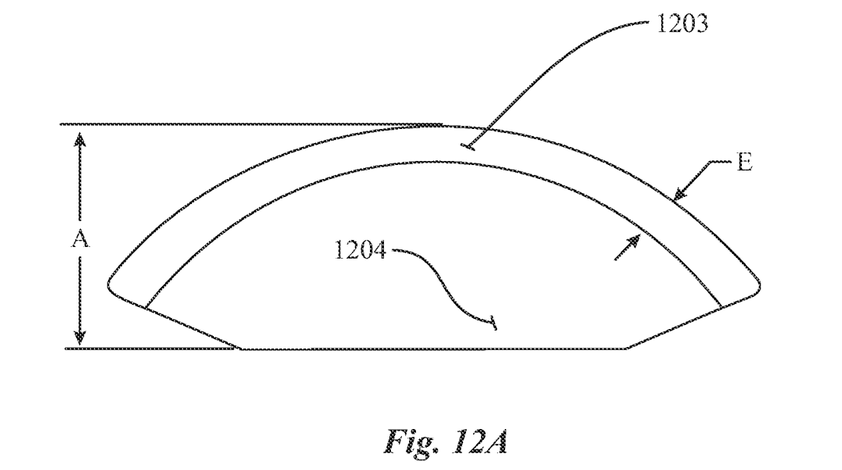
FIG. 12A shows an underside view of an intraoral device bottom plate having an incline angle lip according to another embodiment of the present invention.

FIG. 12A shows an underside view of an intraoral device bottom plate 1204 having a formed lip 1203 provided thereto according to another embodiment of the present invention. Bottom plate 1204 may be an interchangeable bottom plate like bottom plate 1003 described further above although attachment hardware is not illustrated in this embodiment but may be assumed present. Shell form 1002, not illustrated here but described above, may be assumed to be unchanged or unmodified and plate 1204 may be assembled to the shell form using any of the aforementioned means for assembly, such as peg/hole interfaces, tongue and groove interfaces, or the like.

In this embodiment, bottom plate 1204 has the same length dimension A as bottom plate 1003 of intraoral device 1001 of FIG. 10A. Lip 1203 is provided along the anterior curved edge of bottom plate 1204 where an incline maybe actualized having a length E. In this embodiment, the length E of the incline angle produced may be about 3 millimeters the lip 1203 contiguously formed along the anterior curved edge of the bottom plate 1204.

Figure 12B:
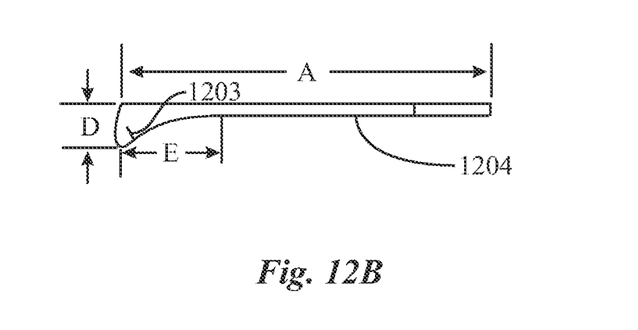
FIG. 12B shows a side view of the bottom plate of FIG. 12A.

FIG. 12B shows a right side view of bottom plate 1204 of FIG. 12A. In this side view, the length A represents the length of the bottom plate 1204, which may be the same dimension as the length of the intraoral device. Length E may be about 3 millimeters but may be more or less than 3 mm without departing from the spirit and scope of the invention. Height dimension D at the anterior curved edge of bottom plate 1204 may be up to 5 millimeters or so. In this embodiment, the interchangeable plates may have different general incline angles from 0 to 20 degrees as previously described above. This interchangeability allows the practitioner to use the same stock shell form with the desired bottom plate added for the particular overbite of a user. Also in this embodiment, the surface of the incline of lip 1203 may be radiused slightly so that forward and lateral movement of mandible incisors do not hit an abrupt edge before advancing onto the incline surface.

The overall goal of this added lip feature is to eliminate any possible interferences in lateral and protrusive movements, while still supporting free movement of the mandible back into centric relation. The general angle of incline for lip 1203 increases and ensures cuspid and anterior guidance in lateral and protrusive movements of the mandible.

FIG. 13A shows a rear elevation view of an intraoral device 1300 with an incline angle lip. Intraoral device 1300 may be similar to the intraoral device of FIG. 12A including the formed lip referenced herein as incline angled lip 1303, which is synonymous to lip 1203 described previously. In this embodiment, the posterior side of the intraoral device 1300 is flat edged as opposed to three sided as depicted above.

Bottom plate 1304 supports the lip 1303 and may be assembled to shell form 1301 as described previously. In this view through 1302 is visible as well as the back wall of the shell form. Shell form 1301 is analogous to shell form 1002 of FIG. 10A with the exception of having a flat edge posterior side.

FIG. 13B shows a bottom view of intraoral device 1300 of FIG. 13A. In this view lip 1303 is formed contiguously along the curved edge of the front of bottom plate 1304. The bottom plate 1304 conforms generally with the shape profile of the intraoral device shell form. It is also noted herein that the intraoral device shell form may or may not include a central floor as the bottom plate may be assembled using installation points strategically spaced about the edge regions of the device. However, the shell form may include a bottom surface that covers the entire footprint of the device without departing from the spirit and scope of the invention and fastening points may be provided within the central space of the footprint without departing from the spirit and scope of the invention. In such an embodiment, the thickness of the bottom plate adds to the thickness of the shell form bottom wall creating a double wall.

It will be apparent with skill in the art that the intraoral device of the present invention may be provided using some or all the elements described herein. The arrangement of elements and functionality thereof relative to the intraoral device of the invention is described in different embodiments each of which is an implementation of the present invention. While the uses and methods are described in enabling detail herein, it is to be noted that many alterations could be made in the details of the construction and the arrangement of the elements without departing from the spirit and scope of this invention. The present invention is limited only by the breadth of the claims below.

The invention claimed is:

1. An intraoral device, comprising;
   a planar surface defined by an arcuate anterior edge and a posterior linear edge;
   an arcuate open channel formed on a first side of the planar surface, the arcuate open channel defined by an anterior wall extending orthogonally from the first side of the planar surface, the arcuate open channel and along the arcuate anterior edge and a posterior wall extending from the 1st side of planar surface, wherein the anterior wall terminates at a top edge and the posterior wall terminating at a second top edge, the top edge and second top edge being parallel and equidistant to each other, the arcuate open channel including dental impression material being adapted to receive planar surface, the arcuate open channel a plurality of maxillary anterior teeth of a user, thereby forming a mold;
   the bottom plate being removably assembled onto a second side of the planar surface the bottom plate conforming to a shape of the planar surface, the bottom plate hosting a first incline angle extending from the posterior linear edge towards the arcuate anterior edge and the first incline angle adapted to engage the incisors of the user;
   wherein the posterior wall transitions from the second top edge away from the arcuate open channel to the posterior linear edge; and wherein the posterior linear edge joins opposed open ends of the arcuate open channel.

2. The intraoral device of claim 1, wherein the bottom plate being interchangeable with a second bottom plate hosting a second inc line angle.

3. The intraoral device of claim 1, wherein arcuate opening channel further configured to receive adjacent maxillary canine teeth of the user.

4. The intraoral device of claim 1, wherein the bottom plate being removably assembled onto the second side of the planar surface by pegs and holes.

5. The intraoral device of claim 1, wherein the first incline angle is contiguous with the bottom plate.

6. The intraoral device of claim 1, wherein the first incline angle is a wedge form centered on the bottom plate, the first incline angle creating a uniform height dimension at the arcuate anterior edge of the planar surface.

7. The intraoral device of claim 2, wherein the bottom plate and the second bottom plate are provided as a set, wherein the first inclined angle being different from the second inclined angle.

8. The intraoral device of claim 7, wherein the first incline angle is twenty five degrees and the second incline angle is five degrees.

* * * * *